June 12, 1973 H. KERRIGAN Plant Pat. 3,356
VARIETY OF AZALEA
Filed Oct. 18, 1971
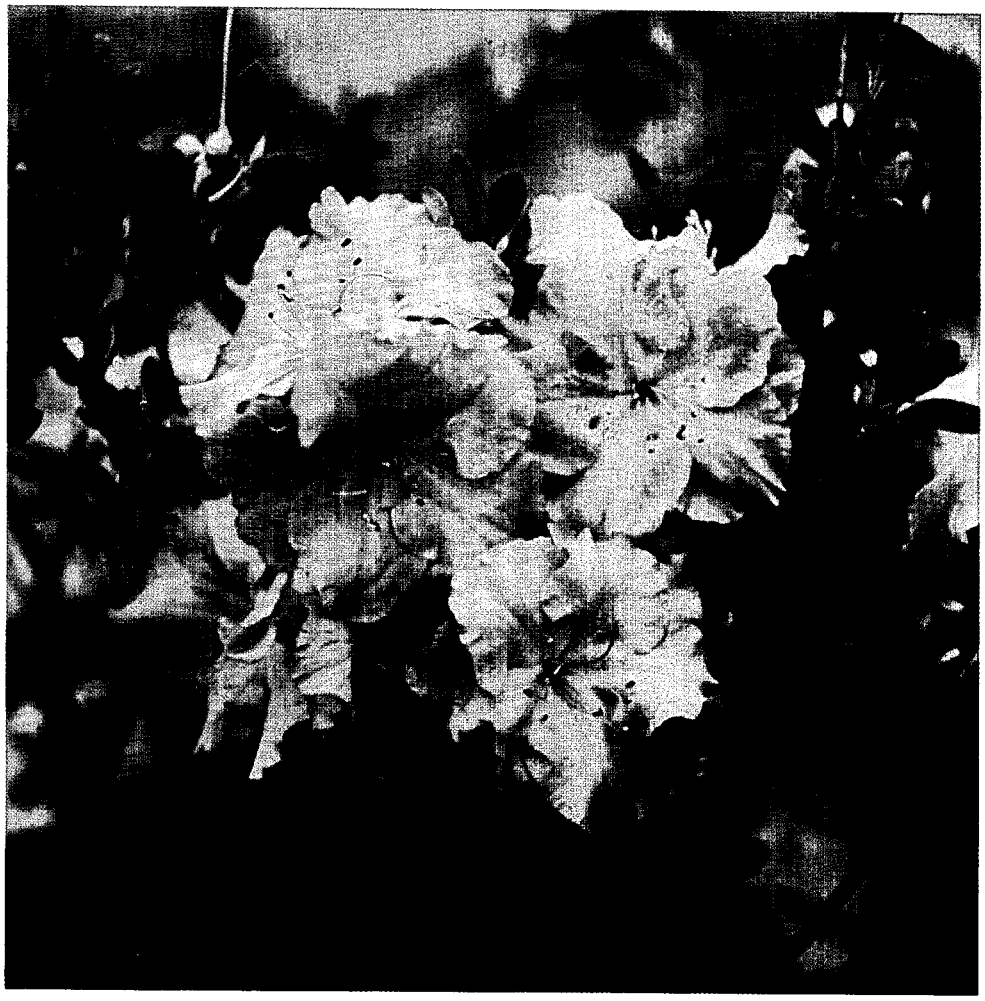

United States Patent Office

Plant Pat. 3,356
Patented June 12, 1973

1

3,356

AZALEA PLANT

Howard Kerrigan, 25783 Mission Blvd., Hayward, Calif. 94544

Filed Oct. 18, 1971, Ser. No. 190,236
Int. Cl. A01h *5/00*
U.S. Cl. Plt.—56 1 Claim

The invention relates to a new and distinct variety of azalea plant of the Belgian-Indica type, originated by me in 1955 as a consequence of a breeding program begun in 1943. The parentage of my new azalea plant is as follows: Goliath (unpatented), the seed parent × Ballerina (P.P. 1,881) the pollen parent.

The object of the cross was to produce a plant of more compact growth habit with larger, more double flowers and the unique color of Ballerina with a later blooming period. These objectives were achieved along with other desirable improvements, as evidenced by the following unique combination of characteristics which are outstanding in the new variety and which distinguish it from its parents as well as from all other varieties of which I am aware. My new variety is primarily characterized by: a combination of large, ruffled, flat, "hose-in-hose" flowers of an unusual shade of apricot pink and a strong, densely compact, low growing plant.

Asexual reproduction of my new variety by cuttings, through a series of annual propagations at Oakland, and Hayward, Calif. in 1958–1969 shows that all characteristics of the variety come true to form through succeeding propagations. The accompanying photographs illustrate the primary characteristics of my new variety of azalea as nearly true as is reasonably possible to make them with presently available techniques. The color references cited are those of the Horticultural Colour Charts of the Royal Horticultural Society.

The following botanical description is based upon observation of one, two, and three year old flowering plants grown at Hayward, Oakland, and Santa Rosa, Calif.

Large, robust, vigorous, compact plant, spreading to 24–36" wide and from 15–24" high at maturity. Branches stout but supple, gently arching. Basal shoots vigorous, about 3/32" in diameter, axillary, branches about 3/32" the first season. Internodes of basal shoots between 5/16 and 3/8" long. Stems erect to almost semi-prostrate; Fern Green (HCC 0862/3) when young becoming brown at the base and becoming gray brown when old. Bark more or less conspicuously striate, young stems bearing prominent chestnut strigae as well as the older wood.

Foliage evergreen of two size classes. Leaves of vigorous growth about 1–1½" long by ½–¾" wide, petiolate, the petioles are about 3/8" long, lamina, elliptic, sparsely pubescent on both surfaces, descending the petiole its entire length. The entire margin is somewhat ciliate, the cilia small, inconspicuous, and chestnut in color. Leaf apex is acute. The leaf midrib is pubescent, especially below. Trichomes are flat, lanceolate, slender, up to 3/32" in length, conspicuous, chestnut, abundant on flower surface, smaller and sparser to the point of becoming almost obsolete on the upper surface of the midrib.

The leaves of the branches of older or more mature wood are smaller, about ½–9/16" long x ¼–3/8" wide with proportionately smaller trichomes, but otherwise similar

2 to the larger leaves. The leaf color is Spinach Green (HCC 0960) above and Spinach Green (HCC 0960/3) below.

The buds of the inflorescence are Lettuce Green (HCC 861/3) the scales are small, about 7/16" long x 3/16" wide, heart shaped to lanceolate, becoming cucullate at anthesis. Pubescence moderate to heavy, small, golden brown, essentially restricted to the rib; however, on the inner scales the pubescence is more widespread and heavier. The scales are scarious to brownish with subhyaline margins and brownish spices at dehiscence.

The inflorescence is 1–2 flowered and umbellate. One flower of the two flowered inflorescence matures at the same time or several days later than the more precocious one and may or may not have slightly shorter peduncles, i.e. if the flowers of the two flowered inflorescence bloom at the same time, the peduncles are of equal length, if not, the later flower has the shorter peduncle. Peduncles are short, slender 3/8–½" long by 1/16–3/32" thick, pubescent and Lettuce Green (HCC 861/3). The pubescence of the peduncle is moderate to dense, hyaline to chestnut; short and silky.

Calyx corolliform, five lobed. The tube of the calyx is about ¾" deep by 1" across, broadly flared. The lobes are 1¼–1½" wide by ¾"–1" long, not variable as to shape and size, sometimes secondarily lobed or incised. The margins are not ciliate but are somewhat fluted giving a ruffled appearance. The reverse of the calyx is Camellia Rose (HCC 622), somewhat streaked with (HCC 622) and freckled with Camellia Rose (HCC 622) on the dorsal two petals. The coloring of the corolla is the same as that of the calyx including the freckle placement and coloring. The tube of the corolla is about ¾" long by ¾" wide at the throat, flaring bilateral symmetrical, slightly gibbous, somewhat higher than broad, and more or less prominently fluted with the midveins depressed. The five corolla lobes are of two size classes. The ventral two are larger, about 1¼–1½" across by 1–1⅛" deep, auriculate. The dorsal three lobes are smaller, about 1–1¼" across by 1–1⅛" deep. The flower is about 2½–2¾" across by 1¾–2" deep.

The stamens are 8–10, modal number 8, filaments slender, white, 1–1¾" long. Anthers small, tan, about 1/32–1/16" long. The pollen is white. The pistil is 1¼–1½" long. Stigma is pale green, capitate, five lobed. Receptive surface divided into five sections, style slender, about 1 3/16–1 7/16" long, curved, not stigmoid, expanded at base to nearly the diameter of the ovary, about 1/16" in diameter at base, 1/32" at the middle. The thickened basal portion of the style pubescent. The pubescence is long, silky, hyaline. The ovary is about 3/16" long by 3/32" wide, heavily pubescent, the pubescence dense, long silky, hyaline.

Having thus disclosed my invention, I claim:

1. A new and distinct variety of azalea plant of the Belgian-Indica type substantially as herein shown and described primarily characterized by: a combination of large, ruffled, flat, "hose-in-hose" flowers of an unusual shade of apricot pink and a strong, densely compact, low growing plant.

No references cited.

ROBERT E. BAGWILL, Primary Examiner